(12) United States Patent
Blair

(10) Patent No.: US 10,329,234 B2
(45) Date of Patent: *Jun. 25, 2019

(54) HETEROGENEOUS METAL-FREE CATALYST

(71) Applicant: UNIVERSITY OF CENTRAL FLORIDA RESEARCH FOUNDATION, INC., Orlando, FL (US)

(72) Inventor: Richard G. Blair, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/670,732

(22) Filed: Aug. 7, 2017

(65) Prior Publication Data

US 2018/0022679 A1 Jan. 25, 2018

Related U.S. Application Data

(63) Continuation of application No. 14/650,537, filed as application No. PCT/US2013/073746 on Dec. 6, 2013, now Pat. No. 9,725,395.

(60) Provisional application No. 61/734,699, filed on Dec. 7, 2012.

(51) Int. Cl.
| | |
|---|---|
| *C07C 5/03* | (2006.01) |
| *C07C 9/08* | (2006.01) |
| *C07C 9/22* | (2006.01) |
| *B01J 27/24* | (2006.01) |
| *B01J 35/02* | (2006.01) |
| *B01J 37/00* | (2006.01) |
| *B01J 37/34* | (2006.01) |
| *C07C 15/16* | (2006.01) |
| *C07C 15/18* | (2006.01) |
| *C07C 45/62* | (2006.01) |
| *C07C 51/36* | (2006.01) |
| *C07C 57/30* | (2006.01) |
| *C01B 21/064* | (2006.01) |
| *C07C 231/00* | (2006.01) |
| *C07C 233/11* | (2006.01) |
| *C07C 253/00* | (2006.01) |
| *C07C 255/03* | (2006.01) |
| *C07C 255/07* | (2006.01) |
| *C07C 49/784* | (2006.01) |

(52) U.S. Cl.
CPC .............. *C07C 51/36* (2013.01); *B01J 27/24* (2013.01); *B01J 35/02* (2013.01); *B01J 37/00* (2013.01); *B01J 37/0036* (2013.01); *B01J 37/343* (2013.01); *C01B 21/0648* (2013.01); *C07C 5/03* (2013.01); *C07C 45/62* (2013.01); *C07C 231/00* (2013.01); *C07C 253/00* (2013.01); *B01J 2231/643* (2013.01); *B01J 2231/645* (2013.01); *C01P 2002/85* (2013.01); *C01P 2004/03* (2013.01); *C07C 2527/24* (2013.01)

(58) Field of Classification Search
CPC ... B01J 27/24; B01J 35/02; B01J 37/00; B01J 37/0036; B01J 37/343; B01J 2231/643; B01J 2231/645; C01B 21/0648; C07C 231/00; C07C 253/00; C07C 45/62; C07C 5/03; C07C 51/36; C07C 2527/24; C01P 2002/85; C01P 2004/03
See application file for complete search history.

(56) References Cited

U.S. PATENT DOCUMENTS 9,725,395 B2 * 8/2017 Blair ...................... C07C 51/36

OTHER PUBLICATIONS

Janesko, "Frustrated Lewis Pair Nanoribbons," J. Phys. Chem. C 2012, 116, 16467-16472.*
Raphael Wischert et al: [gamma]-Alumina: The Essential and Unexpected Role of Water for the Structure, Stability, and Reactivity of "Defect" "Sites", Journal of the American Chemical Society, vol. 134, No. 35, Aug. 3, 2012 (Aug. 3, 2012), pp. 14430-14449, EP55250157.
Hongyu Wu et al: "Metal free hydogenation reaction on carbon doped boron nitride fullerene: A DFT study on the kinetic issue", International Journal of Hydrogen Energy., vol. 37, No. 19, Oct. 1, 2012 (Oct. 1, 2012), pp. 14336-14342, XP055291936.
PCT/US2013/073746—WO/2014/089537—International Search Report and Written Opinion, dated Mar. 25, 2014, 10 pages.
PCT/US2013/073747—Extended European Search Report, dated Aug. 10, 2016, 9 pages.
PCT/US2013/073746—Extended European Search Report, dated Aug. 8, 2016, 12 pages.
Choi, H. et al. J. Am. Chem. Soc. 2011, 133, 2084-2087.
Kang, H.S. J. Phys. Chem. B 2006, 110, 4621-4628.
Peng, G. et al. J. Phys. Chem. 2012, 116, 3001-3006; published Dec. 26, 2011.

* cited by examiner

*Primary Examiner* — Pancham Bakshi
*Assistant Examiner* — Mark R Luderer
(74) *Attorney, Agent, or Firm* — Dunlap Codding, P.C.

(57) ABSTRACT

The inventive concepts disclosed and/or claimed herein relate generally to catalysts and, more particularly, but not by way of limitation, to a heterogeneous, metal-free hydrogenation catalyst containing frustrated Lewis pairs. In one non-limiting embodiment, the heterogeneous, metal-free catalyst comprises hexagonal boron nitride (h-BN) having frustrated Lewis pairs therein.

24 Claims, 9 Drawing Sheets

HETEROGENEOUS METAL-FREE CATALYST

CROSS-REFERENCE TO RELATED APPLICATIONS/INCORPORATION BY REFERENCE STATEMENT

This application is a continuation of U.S. application Ser. No. 14/650,537, filed Jun. 8, 2015, titled HETEROGENEOUS METAL-FREE CATALYST, which is a national stage entry and claims benefit under 35 U.S.C. 371 of PCT/US2013/073746, filed Dec. 6, 2013, which claims benefit under 35 U.S.C. 119(e) of U.S. Provisional Patent Application Ser. No. 61/734,699, filed Dec. 7, 2012, the entire contents of which is hereby expressly incorporated herein by reference.

STATEMENT REGARDING FEDERALLY SPONSORED RESEARCH OR DEVELOPMENT

A portion of this work was sponsored by the Air Force Research Laboratory (AFRL) #FA8650-10-C-2127. The U.S. Government therefore has certain rights in the invention.

BACKGROUND OF THE INVENTIVE CONCEPTS

1. Field of the Inventive Concepts

The inventive concepts disclosed and/or claimed herein relate generally to catalysts and, more particularly, but not by way of limitation, to a heterogeneous, metal-free hydrogenation catalyst containing frustrated Lewis pairs. In one non-limiting embodiment, the heterogeneous, metal-free catalyst comprises hexagonal boron nitride (h-BN) having frustrated Lewis pairs therein.

2. Brief Description of Related Art

The addition of molecular hydrogen ($H_2$) across an unsaturated organic compound such as an olefin is an important step in the processing of petroleum and bio-based chemicals. Although the conversion of olefins to alkanes is thermodynamically favored under appropriate conditions, such reactions are sluggish and a catalyst is required to facilitate hydrogenation. It was first observed that traces of nickel could mediate the addition of $H_2$ to olefins. Later, it was found that palladium, platinum, rhodium, and other precious metals exhibited similar catalytic activity owing to the overlap between these metal's d-orbitals and the molecular orbitals of hydrogen.

Two disadvantages in the use of precious metals such as palladium, platinum, and rhodium are their cost and the potential leaching of such metals into the hydrogenation products. In order to avoid the high costs associated with palladium, platinum, and rhodium containing catalysts, industrial or commercial scale hydrogenation catalysts have generally been nickel-based. Such nickel-based hydrogenation catalysts have been used in a variety of processes, and especially for the hydrogenation of oils. Nickel-based catalyst systems are, however, readily poisoned in operation. While many potential poisons are removed during preprocessing, small quantities still remain, leading to catalyst degradation over time and operation. Additionally, measurable quantities of metal found in the catalyst are incorporated into the final hydrogenation product. The presence of these impurities in the hydrogenation products (or downstream items produced from such hydrogenation products) can have undesirable effects and may have increased toxicity in humans and animals. These and other factors make a nonmetallic or "metal-free" hydrogenation catalyst an attractive alternative for commercial scale hydrogenation processes.

Frustrated Lewis Pair (FLP) catalysts are potentially useful as one type of metal-free catalyst. Catalytic hydrogenation utilizing FLPs as a catalyst material is, therefore, a subject of growing interest because of the opportunity for the development and use of nickel and/or transition-metal-free hydrogenations reactions. In 2007, Stephan and co-workers, for example, developed the first non-transition metal system capable of releasing and absorbing molecular hydrogen using FLPs. Stephan determined that when a sterically encumbered Lewis acid approaches a bulky Lewis base, adduct formation is hindered and gives rise to electronic "frustration". Such frustration effectively mimics the donor-acceptor properties of transition metals. Stephan and his team demonstrated that upon exposure to 1 atm $H_2$ at 25° C., a solution of red phosphino-borane $[(C_6H_2Me_3-2,4,6)_2P(C_6F_4)BF(C_6F_5)_2]$ transformed to the colorless zwitterionic salt $[(C_6H_2Me_3-2,4,6)_2PH(C_6F_4)BH(C_6F_5)_2]$. Upon thermolysis at 150° C., the salt lost $H_2$ and converted back to the original phosphine-borane substrate. Such phosphonium borates (as well as similar compounds) have been shown to successfully catalyze the hydrogenation of select imines, enamines, aldehydes, and olefins.

To date, only homogeneous FLP catalytic systems have been studied, i.e., FLP catalysts and the resulting reactions have previously involved the FLP catalyst being in the same phase as the reactants. For example, the homogeneous FLP catalyst is typically co-dissolved in a solvent with the reactants. Heterogeneous catalysis, on the other hand, is performed with the catalyst in a different phase from that of the reactants. One example of heterogeneous catalysis is the petrochemical alkylation process where the liquid reactants are immiscible with a solution containing the catalyst. Heterogeneous catalysis offers the advantage that products may be readily separated from the catalyst. Typically, heterogeneous catalysts are more stable and degrade much slower than homogeneous catalysts.

In view of the foregoing, there is a need for a heterogeneous, metal-free hydrogenation catalyst having improved stability and separation characteristics. In particular, a heterogeneous, metal-free hydrogenation catalyst having an FLP-type electronic structure would be a valuable addition to catalysts currently available for industrial and commercial use. It is to such a heterogeneous, metal-free hydrogenation FLP catalyst that the presently disclosed and/or claimed inventive concept(s) is directed.

SUMMARY OF THE INVENTIVE CONCEPTS

The inventive concepts disclosed and/or claimed herein generally relate to a heterogeneous, metal-free hydrogenation catalyst. The catalyst comprises a solid surface substantially free of metals, having Lewis acid and Lewis base sites. At least one defect frustrates at least one pair of Lewis acid and Lewis base sites such that the frustrated pair of Lewis acid and Lewis base sites are catalytically active and promote hydrogenation. Methods of preparing and using such a heterogeneous, metal-free hydrogenation catalyst are also taught and disclosed.

BRIEF DESCRIPTION OF THE DRAWINGS

Implementations of the presently disclosed and/or claimed inventive concept(s) may be better understood when consideration is given to the following detailed description thereof. Such description makes reference to the annexed pictorial illustrations, schematics, graphs, and drawings. The figures are not necessarily to scale and certain features and certain views of the figures may be shown exaggerated, to scale, or in schematic in the interest of clarity and conciseness.

(FIG. 8A) $C_2H_4$, (FIG. 8B) $C_2H_6$, and of (FIG. 8C) $C_2H_4$/defective h-BN for surface defect types $B_N$, SW, $V_N$ and $V_B$. Contours are drawn in a linear scale (9 contours from 0 to 0.27 $e/bohr^3$).

DETAILED DESCRIPTION

Figure 1:
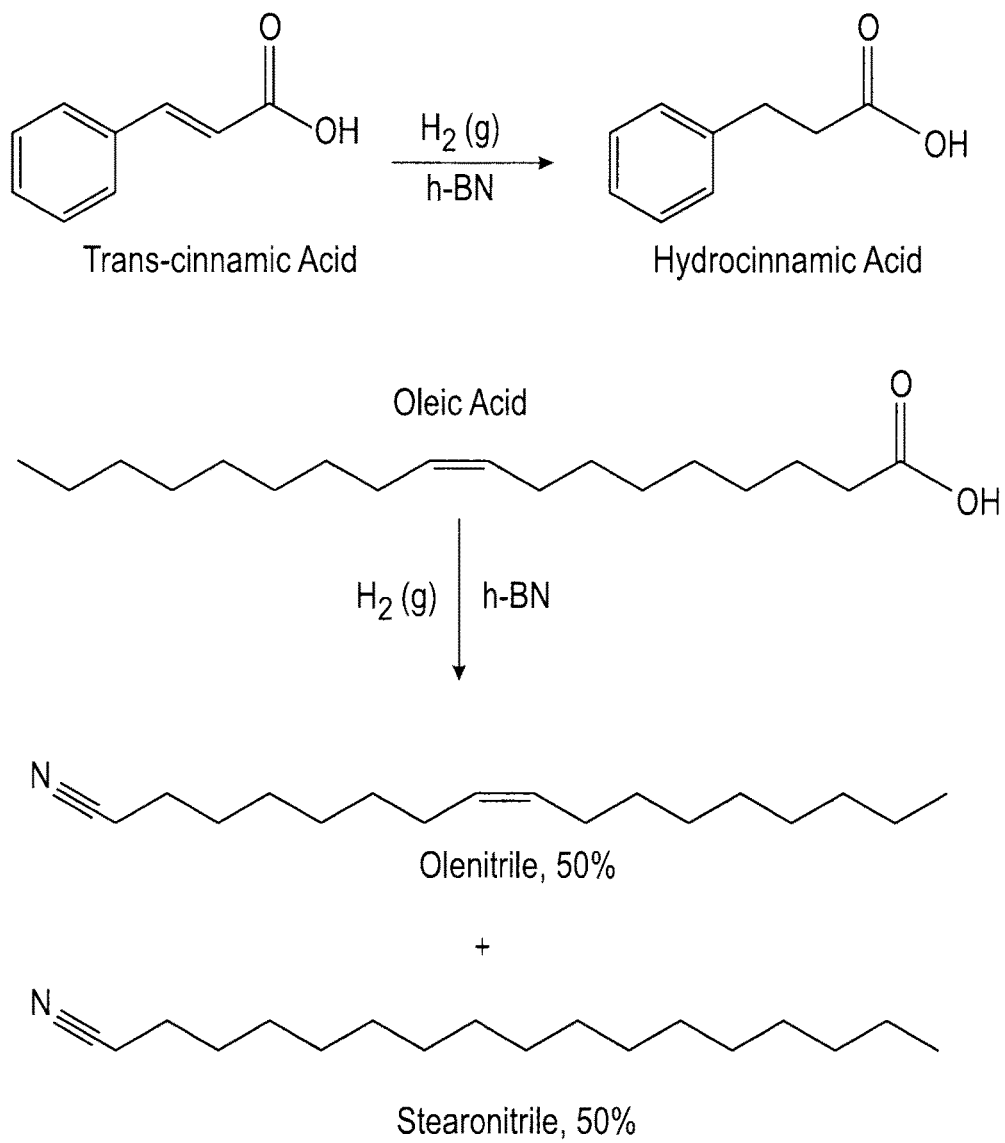
FIG. 1 is a schematic representation of (a) the hydrogenation of trans-cinnamic acid to hydrocinnamic acid over defect laden h-BN catalyst, wherein the h-BN catalyst selectively reduces the olefin moiety, and (b) the hydrogenation of oleic acid to oleonitrile and stearylnitrile.

Before explaining at least one embodiment of the presently disclosed and/or claimed inventive concept(s) herein in detail, it is to be understood that the presently disclosed and/or claimed inventive concept(s) is not limited in its application to the details of construction, experiments, exemplary data, and/or the arrangement of the components set forth in the following description, or illustrated in the drawings. The presently disclosed and/or claimed inventive concept(s) is capable of other embodiments or of being practiced or carried out in various ways. Also, it is to be understood that the phraseology and terminology employed herein is for purpose of description only and should not be regarded as limiting in any way.

In the following detailed description of embodiments of the presently disclosed and/or claimed inventive concept(s), numerous specific details are set forth in order to provide a more thorough understanding of the inventive concept(s). However, it will be apparent to one of ordinary skill in the art that the inventive concept(s) within the disclosure and/or appended claims may be practiced without these specific details. In other instances, well-known features have not been described in detail to avoid unnecessarily complicating the instant disclosure.

Further, unless expressly stated to the contrary, "or" refers to an inclusive "or" and not to an exclusive "or". For example, a condition A or B is satisfied by anyone of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the inventive concept(s). This description should be read to include one or at least one and the singular also includes the plural unless it is obvious that it is meant otherwise.

References to hydrogenation of alkenes are for example only, and the presently disclosed and/or claimed inventive concept(s) can be used with other hydrogenatable compounds. For example, the heterogeneous, metal-free hydrogenation catalyst may be used to reduce or saturate organic compounds having alkyne, aldehyde, ketone, ester, imine, amide, nitrile, and/or nitro functional groups.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

It has been discovered that a solid, heterogeneous hydrogenation catalyst that is substantially free of metals (i.e., that is "metal-free"), can be made from a solid material having a surface with both Lewis acid and Lewis base sites. While not intending to be limited to the chemical mechanism involved, it is believed that the introduction of a defect into the solid material "frustrates" a pair of Lewis acid and Lewis base sites resulting in an active hydrogenation catalyst that can be used in a heterogeneous catalyst system. It is believed that the FLPs create a catalytically active surface functionality that permits chemisorption of hydrogen and chemisorption of a hydrogenatable compound such as an alkene, with a distance between the two sufficient to allow reaction (e.g., hydrogenation) between them to take place.

In one embodiment of the heterogeneous, metal-free hydrogenation catalyst, it has been found that hexagonal boron nitride (h-BN) can produce a heterogeneous FLP under certain novel and non-obvious modifications. Hexagonal boron nitride (h-BN) can be described as a honeycomb network of fused borazine rings. The sheets of h-BN are loosely held together by van der Waals interactions between adjacent boron and nitrogen atoms, which stack in an ABAB fashion.

Pristine sheets of h-BN are exceptionally robust and chemically inert. Hydrogen absorption on the surface of pristine h-BN is endothermic with respect to dissociation but may be enhanced by introducing vacancies or Stone-Wales-type defects into the h-BN sheet. Single layer hexagonal boron nitride sheets can also be thought of as a structurally frustrated Lewis pair. Through delamination and the introduction of other defects in the layers and structure of the materials, the degree of "frustration" within the h-BN molecule can be increased thereby rendering the h-BN material catalytically active. Defects and delamination can be introduced through any known physical chemical, and/or electronic process. In one particular embodiment, such defects can be introduced through the application of mechanical force. When such defects are introduced, for example, the lone electron pairs on the nitrogen are free to interact with adjacent layers, but not with the adjacent boron itself.

As discussed further herein, such h-BN materials having defects giving rise to catalytic activity can be used as hydrogenation catalysts. The h-BN catalyst material, in particular but without limitation, can be used within any known reactor shape or type and may be used with or without a particular refractory material. In one particular embodiment, the h-BN catalyst material is particularly well-suited for use within a mechanical reactor (such as a mill) to catalyze hydrogenation.

Density functional theory (DFT) calculations reveal a 0.56 electron transfer from B to N for defect-free h-BN sheets. Defect-free h-BN behaves, at least theoretically therefore, as an FLP. Computational studies also show that hydrogen absorption on the surface of defect-free h-BN is endothermic with respect to dissociation. Experimental studies have also shown that defect-free h-BN nanotubes can adsorb up to 2.6 mass % of hydrogen. As disclosed herein, the introduction of defects into the structural organization of h-BN results in a material having enhanced FLP structural defects on the surface of the h-BN material. After the introduction of such defects, the h-BN material exhibits catalytic activity and is capable of being used as a hydrogenation catalyst, for example.

The use of defect-free h-BN as a heterogeneous, metal-free hydrogenation catalyst was tested on trans-cinnamic acid. Although a solid at room temperature, trans-cinnamic acid possesses aromatic, aliphatic, and carboxylic hydrogens which may be hydrogenated. Such structure allowed for the study of the selectivity of defect-laden h-BN as a hydrogenation catalyst (i.e., aromatic vs. aliphatic hydrogenation). The carboxylic acid group in the trans-cinnamic acid also provides a chemical environment similar to that found in bio-oils. Defect-laden h-BN sheets catalyze the selective hydrogenation of trans-cinnamic acid to hydrocinnamic acid (see, FIG. 1) and cis/trans isomerization.

Figure 2:
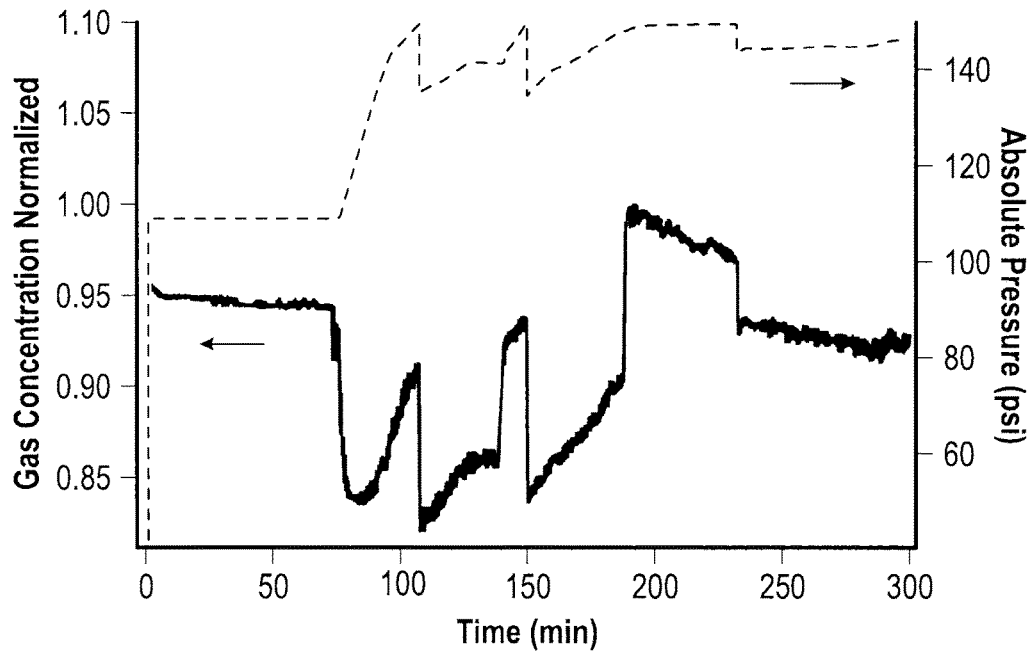
FIG. 2 is a graphical representation of the absolute pressure (top trace—dashed line) and gas concentration (bottom trace—solid line) during the hydrogenation of trans-cinnamic acid over h-BN. The initial pressure increase is due to heating from room temperature to 170° C. The rapid pressure drops are from the pressure control in the hydrogenation apparatus.

In addition to hydrogenation products, decarboxylation, dehydration, and amination products were also found in trace quantities (Table 1) within the reaction products produced when using the defect-laden h-BN as a hydrogenation catalyst with trans-cinnamic acid. Such additional by-products were reduced, however, when the catalyst was recycled—i.e., when an amount of defect-laden h-BN catalyst used in a first reaction was recycled back into a second (or subsequent hydrogenation reaction). Hydrogen uptake, decarboxylation, and dehydration were observed in the pressure changes (FIG. 2) of the reactor during hydrogenation using a defect-laden h-BN material. Initial increases in pressure were observed followed by a slower uptake of hydrogen. Most of the hydrogenation occurred during the first three hours of treatment. The reaction product was a dark-brown liquid. Hydrocinnamic acid yields of 45% where observed with fresh defect-laden h-BN as catalyst and 51% with recycled defect-laden h-BN as catalyst.

Using the same reaction parameters, oleic acid was converted using defect-laden h-BN as catalyst (FIG. 1). The reaction product was determined to be a mixture of oleonitrile (50%) and stearylnitrile (50%). As oleic acid has a much lower viscosity than molten trans-cinnamic acid, the oleic acid also acted as a lubricant during mechanical milling and resulted in the formation of the nitriles by edge attack of the defect-laden h-BN catalyst material followed by dehydration.

Hydrogenation over stainless steel (i.e., through the use of a stainless steel catalyst) has recently been observed. (See, F. Zhao, Y. Ikushima, M. Arai, "Hydrogenation of 2-butyne-1,4-diol to butane-1,4-diol in supercritical carbon dioxide." Green Chem. 5, 656 (2003)). In order to eliminate the possibility that the hydrogenation reactions using defect-laden h-BN catalyst material (as disclosed herein) were influenced or catalyzed by the stainless steel reactor components, exemplary catalysis reactions were performed using stainless steel components in the absence of defect laden h-BN (I.e., dh-BN) catalyst material. Limited hydrogenation was observed when stainless steel milling media was utilized without the h-BN catalyst material—i.e., the stainless steel components contributions to catalytic activity were minor.

TABLE 1

Product distribution by GC peak area of the 5 most abundant products in the hydrogenation of trans-cinnamic acid over defect laden h-BN and recycled defect laden h-BN.

| Product | Structure | First Run | Recycled | Route |
| --- | --- | --- | --- | --- |
| Hydrocinnamic acid | 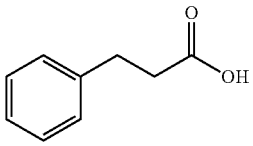 [SMILES: O=C(O)CCc1ccccc1] | 40.50 | 55.31 | Hydrogenation |

TABLE 1-continued

Product distribution by GC peak area of the 5 most abundant products in the hydrogenation of trans-cinnamic acid over defect laden h-BN and recycled defect laden h-BN.

| Product | Structure | First Run | Recycled | Route |
|---|---|---|---|---|
| trans-Cinnamic acid | 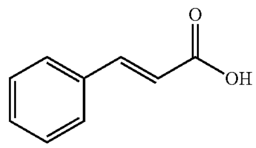 [SMILES: O=C(O)/C=C/c1ccccc1] | 9.60 | 32.45 | |
| Ethylbenzene | 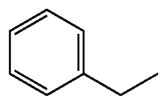 | 7.40 | 0.33 | decarboxylation then hydrogenation |
| Phenyl-propanamide | 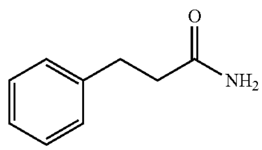 [SMILES: NC(=O)CCc1ccccc1] | 6.00 | 2.36 | hydrogenation, reaction with edge nitrogen atoms then dehydration |
| 1-Penten-3-one, 1,5-diphenyl- | 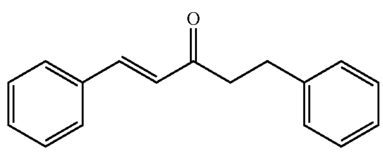 [SMILES: O=C(/C=C/c1ccccc1)CCc1ccccc1] | 2.20 | 0.23 | formation of acid anhydride with hydrocinnamic acid then decarbonylation |

As disclosed, the controlled introduction of defects into h-BN produces a reliable and effective heterogeneous, metal-free hydrogenation catalyst. In particular, but not by way of limitation, mechanical processing (e.g., grinding within a mill or through sonochemical processing) produces a defect-laden h-BN material that has catalytic activity—i.e., a heterogeneous, metal-free hydrogenation catalyst. Mechanical processing may, in one embodiment, be required for the initial preparation of the defect laden h-BN. Grinding h-BN in the presence of hydrogen, for example, induced hydrogenation in a small batch reactor. However, hydrogenation over defect laden h-BN can be performed in a fixed bed reactor or other equipment known to those skilled in the art.

The presently disclosed and/or claimed heterogeneous, metal-free hydrogenation catalyst is not limited to defect laden h-BN. Any solid structure containing a non-metallic Lewis-acid type moiety and a non-metallic Lewis-base type moiety can be used provided that the acid and base moieties are geometrically constrained so that an acid-base adduct cannot form. Non-limiting examples of suitable non-metallic Lewis-acid type moieties include elements from Group 13 in a trigonal planar configuration, higher halides of Group 15 elements, and electron poor π-systems, such as substitutionally doped graphite or carbon nitride. Non-limiting examples of suitable non-metallic Lewis-base type moieties include simple anions such as fluoride and hydride; lone-pair-containing species, such as Group 15 and Group 16 elements; complex anions such as sulfate, selenate, and tellurate; and electron rich π-system Lewis bases, such as substitutionally doped graphite or carbon nitride. Examples of solids that would possess these properties include, but are not limited to, defect laden h-BN, substitutionally doped graphite, substitutionally doped carbon nitride, and inorganic-organic hybrid materials that contain both Lewis acid and Lewis base structures that are constrained from forming an acid-base adduct by the inorganic framework.

Without wishing to be held to any particular hypothesized mode of action, hydrogenation over the defect laden h-BN is believed to occur due to one or more of the following mechanisms: (i) through migration of protons over the catalyst surface, as observed in metal-catalyzed hydrogenation, (ii) through chemisorption of the reactant onto a protonated site, as observed in zeolite-catalyzed hydrogenation, and (iii) through the interaction of bound reactants on separate sheets of dh-BN. All of these mechanisms require the presence of defects for the initial chemisorption of hydrogen.

Figure 3:
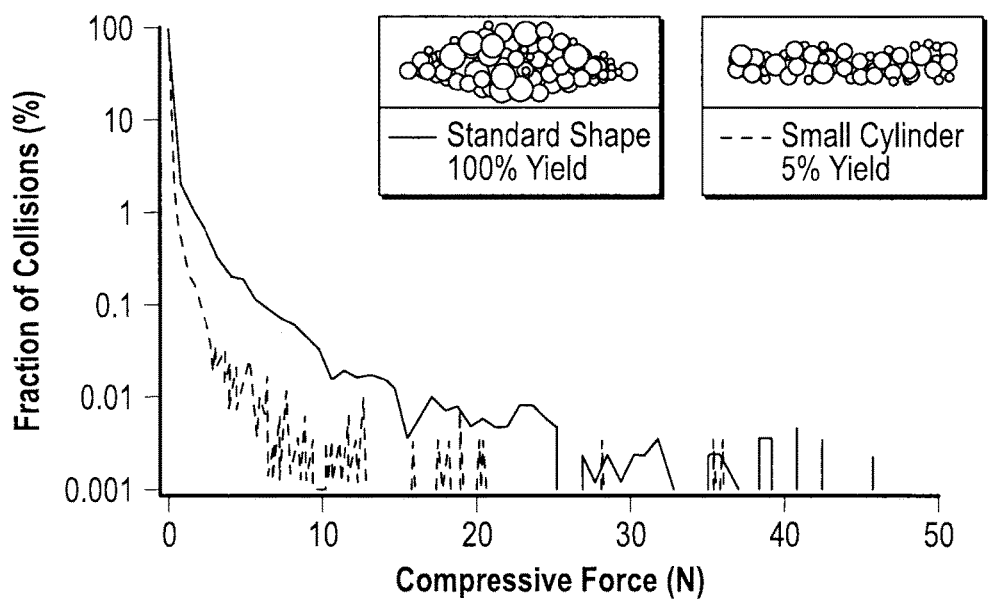
FIG. 3 is a graphical representation illustrating discrete element models that show that compressive forces achievable in our reactor are dependent on the milling intensity. The small cylinder utilized less media and had a smaller volume. This produced lower compressive forces and a lower hydrogenation yield (5% hydrogenation of chalcone after 24 hours). Higher forces are obtained using more media and a larger volume (standard shape). Improved hydrogenation was observed (100% hydrogenation of chalcone after 24 hours).

The first mechanism, i.e., hydrogenation through the migration of protons over a catalyst, requires mobile defects in the catalyst since protons will be bound to the defect sites. The mobility of protons after hemolytic bond cleavage may proceed via a mechanism similar to the diffusion of hydrogen on a graphene sheet. See Herrero et al., "Vibrational properties and diffusion of hydrogen on graphene" Phys. Rev. B: Condens. Matter Mater. Phys., 2009, 79(11): p. 115429/1-115429/8, hereby incorporated by reference in its entirety. Using a basic bond enthalpy analysis, this mechanism would require as much energy as diffusion of H on graphene which proceeds by breaking and creation of C—H bonds (C—H, 337.2 kJ/mol, B—H 330 kJ/mol, N—H 339 kJ/mol) and be less favored when compared to nickel surfaces (Ni—H 289 kJ/mol). Additionally, the $V_N$ defects are not mobile but the $V_B$ defects are mobile above 840K and the B/N and Stone-Wales defects are mobile under plastic deformation. See Alem et al., "Vacancy growth and migration dynamics in atomically thin hexagonal boron nitride under electron beam irradiation." Physica Status Solidi Rapid Research Letter, 2011. 5(i): pp. 295-297; Zobelli et al., "Vacancy migration in hexagonal boron nitride." Phys. Rev. B: Condens. Matter Mater. Phys., 2007. 75(9): pp. 094104/1-094104/7; and Zhang et al., "Diffusion and coalescence of vacancies and interstitials in graphite: A first-principles study." Diamond & Related Materials, 2010. 19: pp. 1240-1244, each of which is hereby incorporated by reference in its entirety. The motion of defects in BN nanotubes has been observed under applied load and the forces generated during milling are sufficient to exceed the compressive yield strength of h-BN (41.3 MPa) when milling intensity is high enough (See FIG. 3);

The second mechanism, i.e., hydrogenation through chemisorption of the reactant onto a proton-laden defect, can occur without the application of mechanical force. Similar to the diffusion of protons over the dh-BN surface mechanism, as described above, no change in the catalytic efficiency would be expected when using dh-BN as a hydrogenation catalyst without the input of mechanical energy.

The third mechanism, i.e., hydrogenation through the interaction of bound reactants on separate sheets of dh-BN, can occur when a bound olefin on a dh-BN sheet interacts with a bound hydrogen on a separate dh-BN sheet when the two sheets come in close proximity due to mixing.

Commercial use of the presently disclosed and/or claimed inventive concept(s) heterogeneous, metal-free hydrogenation catalysts will lower the costs associated with traditional hydrogenation catalysts and improve the quality of the product. Such use will also eliminate the incorporation of metal into the final product. The elimination of metals in hydrogenation products will positively affect public health, since many of the hydrogenated fats used in foods are produced using a nickel catalyst. The United States has abundant supplies of boron, but limited reserves of nickel, palladium, platinum, and rhodium. The use of h-BN catalysts will, therefore, reduce the United States dependency on these precious metals and improve the quality and fitness for consumption of hydrogenated products.

The presently disclosed and/or claimed inventive concept(s) encompasses the use of heterogeneous, metal-free hydrogenation catalysts for the production of biofuels, the production of hydrogenated oils and fats, upgrading of both petroleum and bio-based fuels, the production of plastics, as well as the production of pharmaceuticals. The use of the heterogeneous, metal-free hydrogenation catalysts have, therefore, significant commercial value.

Examples

Figure 4:
FIG. 4 is a SEM image of defect laden h-BN produced by mechanochemical intercalation and reaction with lithium metal. Clusters and single-sheets of h-BN can be seen, with a few layer sheets adopting a scroll-like secondary structure.

In one exemplary embodiment, a hydrogenation reactor can be constructed in a manner similar to a pebble mill. Such a pebble mill is capable of producing defect laden h-BN by mechanically inducing defects and delamination of the physical structure of h-BN. The continuous grinding motion within the mill prevents cluster formation and maximizes the number of few-layer sheets of h-BN. In order to verify the presence of defect-laden sheets, scanning electron microscopy (SEM) was used to characterize the morphology of the defect laden h-BN catalyst. Few-layer sheets are observed by SEM and appear to form tubular structures or nano-scrolls as seen in FIG. 4.

In order to gauge the hydrogenation ability of defect-laden h-BN in a heterogeneous catalytic reactor system, trans-cinnamic acid was chosen as a substrate as the compound possesses aromatic, olefinic, and carboxylic moieties. Non-selective hydrogenation of trans-cinnamic acid results in the complete hydrogenation of the molecule such as occurs with Raney nickel, which produces 3-cyclohexane-propionic acid from trans-cinnamic acid. The presence of carboxylic groups within trans-cinnamic acid also allows for the characterization of hydrogenolytic activity as well. Oleic acid is a good model for biodiesels which require hydrogenation to improve storage life. Defect laden h-BN material possesses several potentially active sites—i.e., the defect laden h-BN material contains defect sites in both sheet and edge sites and thereby is particularly useful as a heterogeneous, metal-free hydrogenation catalyst.

Figure 6:
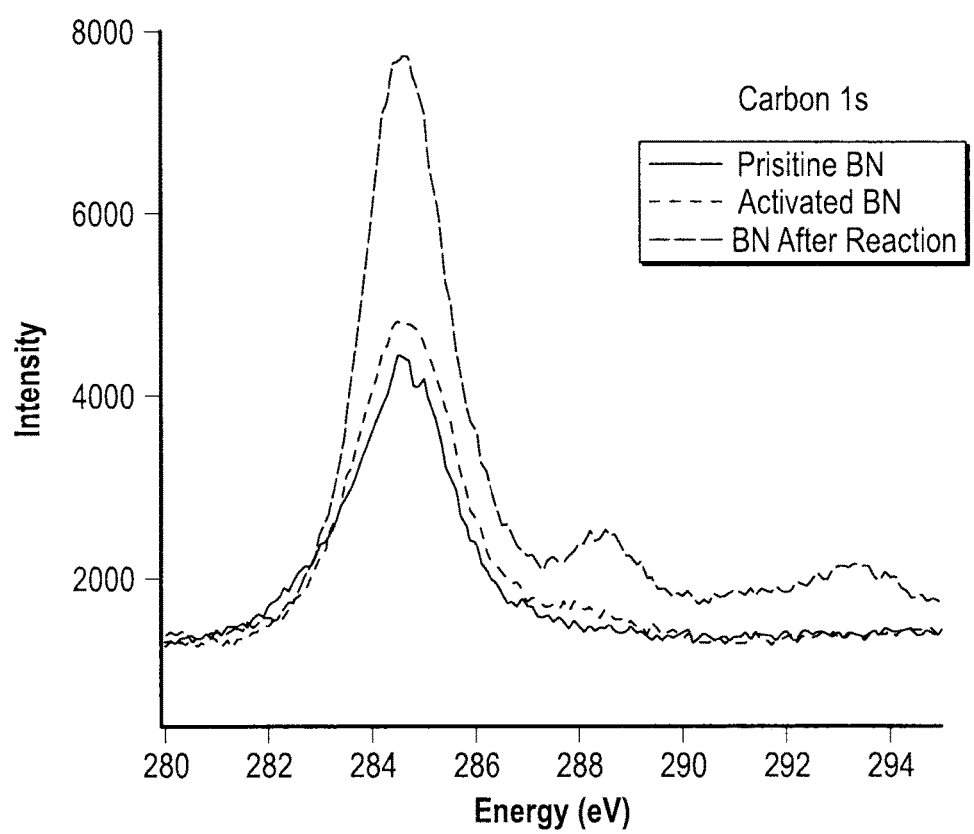
FIG. 6 is X-ray photoelectron spectra of the carbon 1s region of h-BN as received (bottom trace—solid line), after inducing defects (middle trace—smaller dashed lines), and after use as a hydrogenation catalyst (top trace—longer dashed lines). Carbon incorporation is evident even after thorough washing with $CH_2Cl_2$.

Using a defect-laden h-BN material, hydrogenation products, along with decarboxylation and amination products, were produced. Although trans-cinnamic acid is known to undergo decarboxylation at elevated temperatures, a recycled catalyst comprising defect-laden h-BN produced less of such by-products. Such a finding is indicative that the observed decarboxylation products were not formed by the thermal decarboxylation of trans-cinnamic acid alone. As such, these by-products were produced by reaction with edge nitrogen atoms in the defect-laden h-BN catalyst material. There is necessarily a lower concentration of edge nitrogen atoms in a recycled catalyst which may explain the lower production of experimentally produced by-products. XPS analysis of the catalyst after hydrogenation confirmed the presence of carbon (FIG. 6).

The application of mechanical force is, in one embodiment, a preferred method for the delamination and formation of defects in the h-BN catalytic material. Such a delaminating and defect forming force can be applied during the step of hydrogenation or may be utilized as a pretreatment step since the defect sites are stable up to 900° C. (See, P. Wang, S. Orimo, T. Matsushima, H. Fujii, G. Majer, "Hydrogen in mechanically prepared nanostructured h-BN: a critical comparison with that in nanostructured graphite." Applied Physics Letters 80, 318 (2002)). The application of force during milling requires the efficient transfer of mechanical force to the h-BN catalyst material.

The initial steps of hydrogenation on a catalytic substrate of an olefin are chemisorption, followed by reduction of the C—C bond order in the chemisorbed molecule. In order to understand this process with respect to the use of the h-BN catalyst material, it is useful to evaluate the binding energies and electronic structure of the trans-cinnamic acid molecule on the defect laden h-BN catalyst material. Ethene ($C_2H_4$), the simplest possible molecule with such a bond, was investigated as a model for the olefinic carbons in trans-cinnamic acid. First-principles electronic structure calculations of a $C_2H_4$ molecule on a single h-BN layer were employed by utilizing the van der Waals density functional (vdW-DF). According to the experimental results, $C_2H_4$ does not chemisorb on defect laden h-BN catalyst material.

Figure 5:
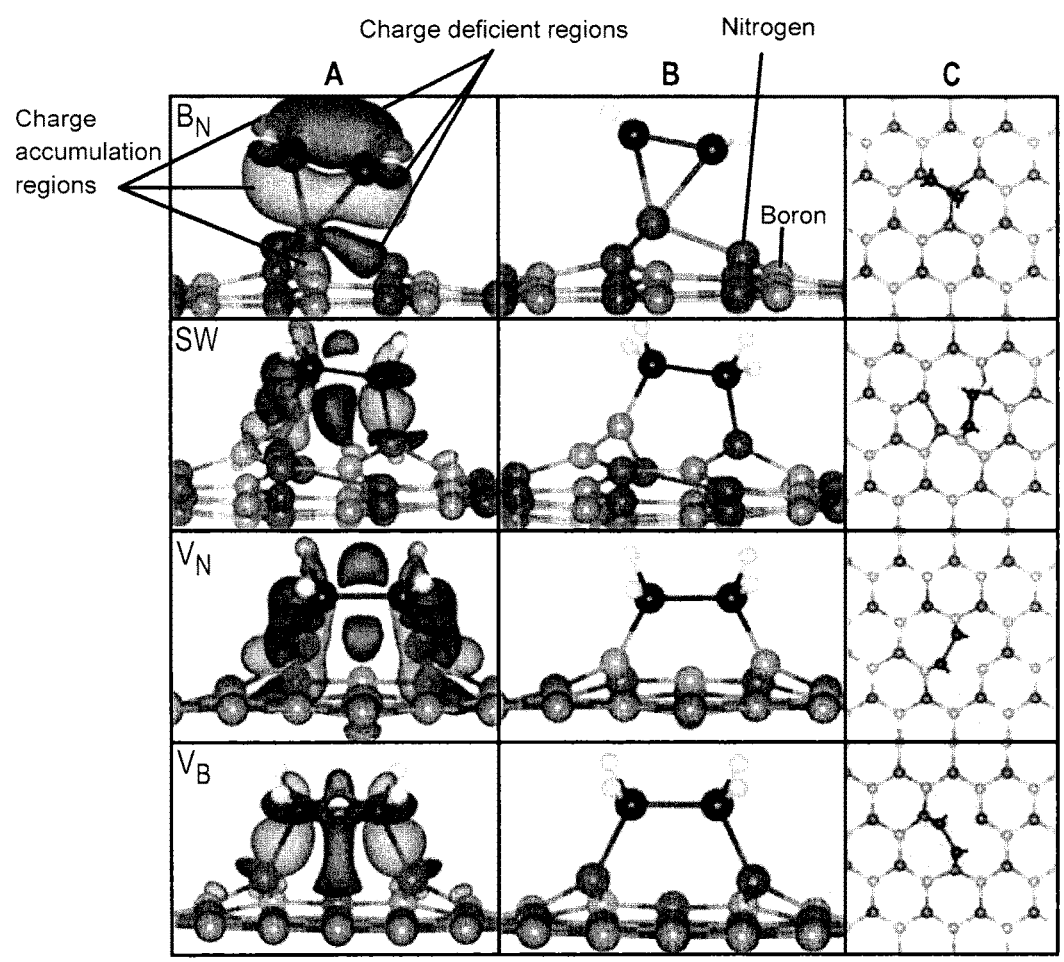
FIG. 5 is a graphical representation of (A) Charge-density redistribution after the adsorption of $C_2H_4$ molecule on $B_N$, SW, $V_B$, and $V_N$ defects in a h-BN substrate. Isosurfaces are drawn at 0.01 $e/Bohr^3$. The charge deficit and accumulation regions are identified therein, wherein charge flow from the charge deficit region to the charge accumulation region. A side view (B) and a top view (C) of the respective configurations is provided without the charge density being indicated for purpose of clarity.
Figure 7:
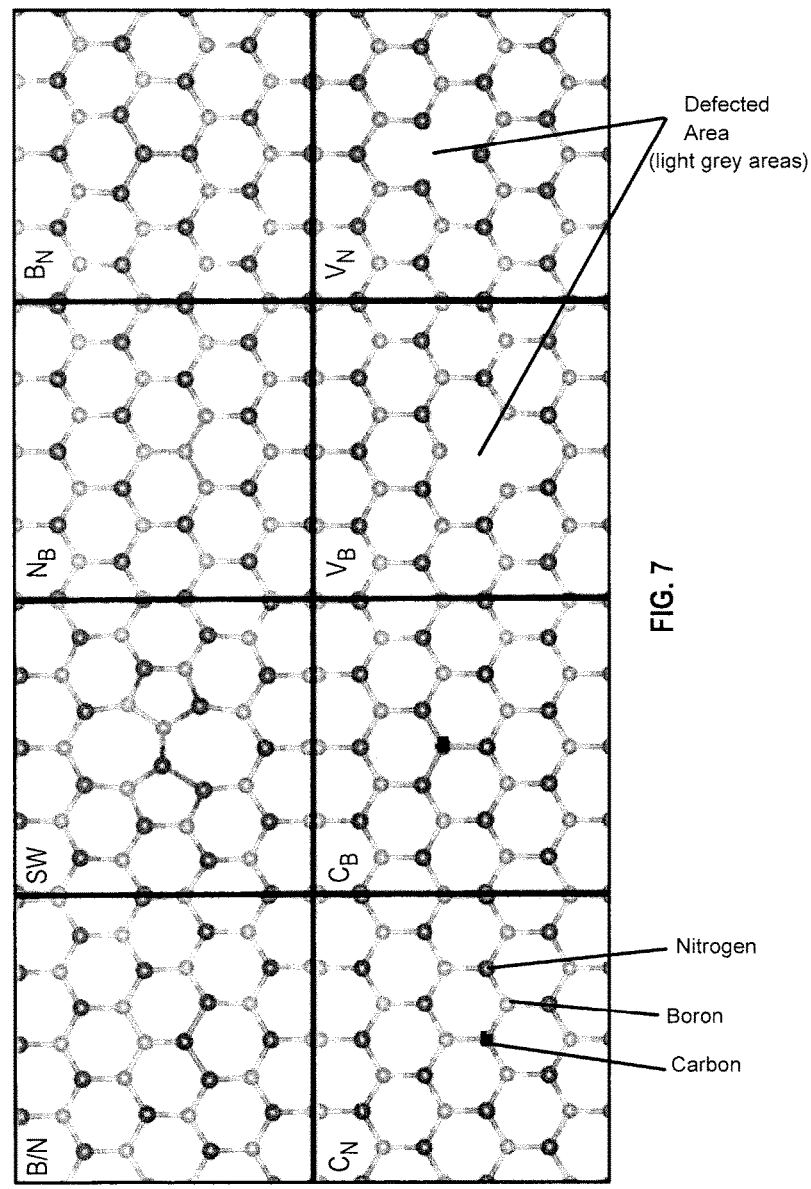
FIG. 7 is a graphical representation of a top view of different defect structures created in h-BN. These are (from top left to bottom right): 180° rotation of a BN bond (B/N), 90° rotation of a BN bond Stone-Wales defect (SW), nitrogen substitution for boron (NB), boron substitution for nitrogen (BN), carbon substitution for nitrogen (CN), carbon substitution for boron (CB), boron vacancy (VB), and a nitrogen vacancy (VN). The light-gray backgrounds indicate the defected areas.

Given that point defects generally favor hydrogen chemisorption, it was expected that point defects in h-BN sheets (i.e., the h-BN catalyst material) would also promote ethene chemisorption. The adsorption and electronic structure of the $C_2H_4$ molecules on eight (8) types of defects in defect-laden h-BN was modeled and the results are illustrated in FIG. 7. The binding energies of ethene on h-BN sheets with these same eight (8) defects are presented in Table 2. Chemisorption occurs on h-BN sheets with four types of defects: boron substitution for nitrogen ($B_N$), Stone-Wales defects (SW), boron vacancies ($V_B$), and nitrogen vacancies ($V_N$). The binding energies (in eV) of $C_2H_4$ on h-BN sheets with these defects are −1.95, −0.23, −3.71, and −1.90, respectively. The top and side views of these systems are shown in columns B and C of FIG. 5.

The charge density redistribution of the system was calculated using the following formula: $\Delta n(\vec{r}) = n_{System}(\vec{r}) - [n_{Mol}(\vec{r}) + n_{BN}(\vec{r})]$; where $n_{System}(\vec{r})$, $n_{Mol}(\vec{r})$, and $n_{BN}(\vec{r})$ are the charge density of the system, the charge density of the $C_2H_2$ molecule, and the charge of density of the h-BN sheets with defects, respectively. Column A in FIG. 5 demonstrates the increased charge density between the $C_2H_4$ molecule and the defect-laden h-BN substrate. The charge enhanced regions located between the carbon atoms and the substrate atoms indicate chemical bonding. The charge deficient regions between two carbons coincide with the π-bond in an isolated $C_2H_2$ molecule indicating the loss of charge from π-bond and a decrease in the C—C bond order. In the case of the SW, $V_N$ and $V_B$ defects, the charge from the original π-bond is mostly removed from the area between the two carbons. In these cases, it can be concluded that the π-bond is broken. Since in the h-BN substrate there is still some charge between the two carbons, it can be concluded that the double bond is partially weakened.

Figure 8A:
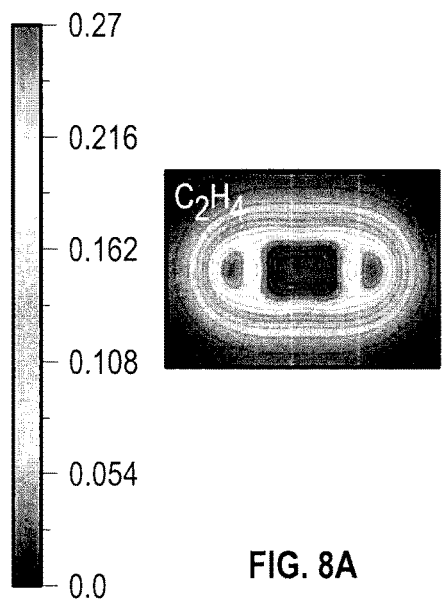
FIGS. 8A, 8B, and 8C are graphical representations of vertical plane cross-sections, passing through the center of the two ethene carbon atoms, of the total charge density of gas-phase.
Figure 8B:
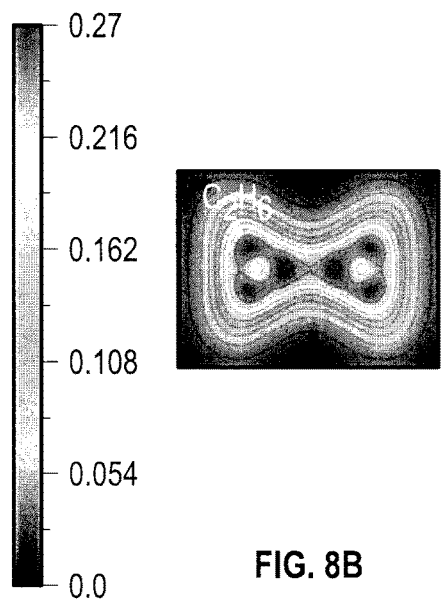
Figure 8C:
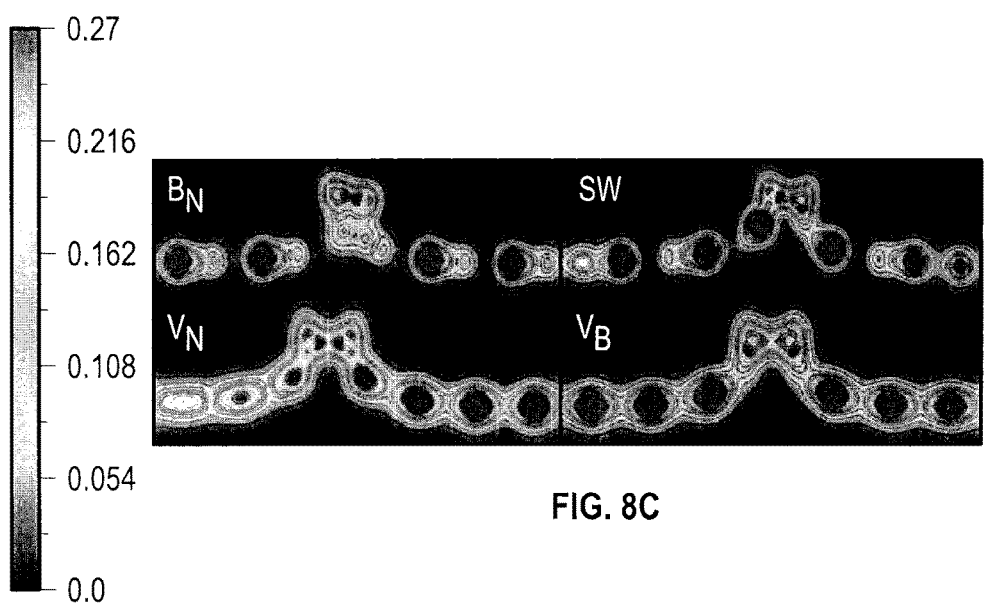

The effect these defects have on the carbon double bond can be determined by analyzing their effect on hybridization. A comparison of the charge density along a vertical plane passing through the two C atoms compared to those for gas-phase $C_2H_4$ and $C_2H_6$ illustrates the h-BN substrate's effect (FIGS. 8A, 8B, and 8C). When $C_2H_4$ adsorbs on a defect in the h-BN sheet, its C atoms partially retain their original $sp^2$ hybridization (C=C), but when it adsorbs on a SW, VB, or VN h-BN defective site, its C atoms rehybridize to $sp^3$ (C—C), facilitating hydrogenation and desorption of $C_2H_6$.

The following exemplary synthesis, use, and analysis of defect laden h-BN as a heterogeneous metal-free hydrogenation catalyst is provided as a non-limiting example of the presently disclosed and/or claimed inventive concept(s) provided herein.

Synthesis of Defect Laden h-BN

Defect laden h-BN was prepared according to two differing methods. In the first method, pristine h-BN (Grade PCTFS, Saint-Gobain Ceramic Materials) was dried at 180° C. under dynamic vacuum and transferred to an argon-filled glovebox. Approximately 2 grams of h-BN was mixed with 0.200 g of lithium (99.9%, Alfa Aesar) and reacted via high-energy ball milling in an 8000M and/or 8000D SPEX Certiprep mixer/mills. Milling vials were constructed from 440C stainless steel with an approximate volume of 65 ml. Buna-N quad O-rings were used to maintain a seal during milling. Kinetic energy was supplied for 30 minutes with one 0.5" stainless steel ball weighing approximately 8.0 g. After 30 minutes, two additional 0.5" stainless steel balls were added and the reaction was milled for an additional 7.5 hours. The resulting lithiated solid was subsequently hydrolyzed using excess $H_2O$ to remove $Li_3N$ producing vacancies in the h-BN sheets. The morphology of this defect laden h-BN was examined via scanning electron microscopy (SEM) performed on a Tescan Vega SBH operating at 30 kV. (FIG. 4)

Alternatively, 20 grams of dry h-BN was loaded into a custom pebble mill with the milling container constructed of 304 stainless steel. Spherical milling media (440C) was added in the following quantities and sizes: (12) 0.75" balls, (27) 0.5" balls, and (50) 0.25" balls. The mill was run at 60 rpm for 96 hours under 120 psi of UHP hydrogen. The milling vial was transferred to an argon-filled glovebox and the prepared catalyst powder was removed and stored until needed.

Hydrogenation

Hydrogenation was performed in a custom pebble mill with a gas-tight milling container constructed of 304 stainless steel. The reaction vessel was shaped as a double truncated cone to ensure adequate tumbling of the milling media. Conflat flanges with silicone O-rings and Deublin rotary feedthroughs with Kalrez O-rings and Krytox lubricant were used to maintain gas tight conditions during operation. Stainless steel frits (Applied Porous Materials) were fitted to the entry and exit feedthroughs to eliminate the accumulation of dust in the sealing surfaces of the feedthroughs. Spherical milling media (440C) was added in the following quantities and sizes: twelve (12) 0.75" balls, twenty-seven (27) 0.5" balls, and fifty (50) 0.25" balls. Temperature was controlled with an Omega CN3000 process controller and a K-type thermocouple spring mounted to the inlet flange. Heat was applied by a wound NiChrome heating element embedded in shaped firebrick. Pressure was monitored with a NOSHOK pressure transducer and controlled with a MicroMod 53MC5000 loop controller. The mill's rotational speed was controlled with a ⅓ hp variable speed DC motor. Hydrogenation reactions were carried out at temperatures up to 170° C., pressures between 150 and 50 psi, and rotary speeds of 60 rpm. Hydrogenations were performed with 20 grams of substrate and 2 grams of defect laden h-BN. Two substrates were investigated: trans-cinnamic acid (Eastman, Practical Grade) and oleic acid (Fisher Scientific, Lab Grade).

Gas Chromatography with Mass Sensitive Detection

GC-MS analysis was performed on an Agilent 6850 GC with an Agilent 19091-433E HP-5MS column (5% phenyl methyl siloxane, 30 m×250 μm×0.25 μm nom.) coupled with a 5975C VL mass selective detector. Samples were pulled from the reactor, dissolved in dichloromethane and filtered through a Whatman 0.2 μm PTFE syringe filter before injection. Quantitation of the trans-cinnamic acid hydrogenation products was performed by using external standard solutions of trans-cinnamic acid (Eastman, Practical Grade) and hydrocinnamic acid (Acros Organics, 99%) in dichloromethane.

XPS

X-ray photoelectron spectra were recorded on a Physical Electronics 5400 photoelectron spectrometer with a magnesium source. The spectra of the carbon 1s region is presented in FIG. 6.

Computational Details

Density functional theory (DFT) calculations were performed to evaluate the binding energies and electronic structure of the $C_2H_4$ molecule on defected boron nitride single layers employing the formalism of the van der Waals density functional (vdW-DF) (See, M. Dion, H. Rydberg, E. Schröder, D. C. Langreth, B. I. Lundqvist, "Van der Waals Density Functional for General Geometries." Physical Review Letters 92, 246401 (2004); and T. Thonhauser et al., "Van der Waals density functional: Self-consistent potential and the nature of the van der Waals bond." Physical Review B 76, 125112 (2007)) as implemented in the VASP code (See, G. Kresse, J. Furthmüller, "Efficiency of ab-initio total energy calculations for metals and semiconductors using a plane-wave basis set." Computational Materials Science 6, 15 (1996); G. Kresse, J. Furthmüller, "Efficient iterative schemes for ab initio total-energy calculations using a plane-wave basis set." Physical Review B 54, 11169 (10/15/, 1996); G. Kresse, J. Hafner, "Ab initio molecular dynamics for liquid metals." Physical Review B 47, 558 (1993); and G. Kresse, J. Hafner, "Ab initio molecular-dynamics simulation of the liquid-metal-amorphous-semiconductor transition in germanium." Physical Review B 49, 14251 (1994)).

In this formalism, the exchange-correlation energy is calculated as: $E_{XC}=E_{GGA}^X+E_{lc}^C+E_{nlc}^C$; where $E_{GGA}^X$ is a semi-local exchange functional from the revised generalized-gradient approximation (GGA) in the form of the Perdew-Burke-Ernzerhof functional (revPBE) (See, Y.

Zhang, W. Yang, Comment on "Generalized Gradient Approximation Made Simple". Physical Review Letters 80, 890 (1998)), $E_{lc}^C$ is a local correlation energy described within the local density approximation, $E_{nlc}^C$ is the nonlocal correlation energy as described by Dion (See, M. Dion, H. Rydberg, E. Schröder, D. C. Langreth, B. I. Lundqvist, "Van der Waals Density Functional for General Geometries." Physical Review Letters 92, 246401 (2004)). The efficient algorithm proposed by Román-Pérez and Sole (See, G. Román-Pérez, J. M. Soler, "Efficient Implementation of a van der Waals Density Functional: Application to Double-Wall Carbon Nanotubes." Physical Review Letters 103, 096102 (2009)) is used to reduce the computation effort. The projector augmented wave (PAW) scheme (See, P. E. Blöchl, "Projector augmented-wave method." Physical Review B 50, 17953 (1994); and G. Kresse, D. Joubert, "From ultrasoft pseudopotentials to the projector augmented-wave method." Physical Review B 59, 1758 (1999)) is utilized with the potentials taken from the potential-library provided with VASP. The electronic wave functions were expanded in a plane wave basis set with a cutoff of 500 eV. A single k-point (Gamma) was found to be sufficient to sample the Brillouin zone of a (6×6) BN slab with 15 Å vacuum on top of it. The systems were optimized so that all force components acting on each atoms are smaller than 0.01 eV/Å. The lattice parameters of h-BN were optimized to be 2.523 Å (in agreement with experimental value of 2.505 Å (37).)

Defect Structures

The ethene molecule does not bind on h-BN sheets so point defects produced in h-BN sheets promote the chemisorption of $C_2H_4$ on h-BN sheets. Eight (8) defects in the h-BN sheets were studied (as shown in FIG. 7).

Binding Energies

Binding energies of all eight (8) defects are presented in Table 2. The binding energy is calculated using the formula: $E_{BE}=E_{System}-(E_{Mol}+E_{BN})$; where $E_{System}$, $E_{Mol}$, and $E_{BN}$ are the total energy of the molecule on the substrate, the molecule alone, and of the defective h-BN substrate, respectively. The more negative the binding energy, the stronger the chemisorption of $C_2H_4$ on the defective BN sheets. Ethene is chemisorbed on four types of defect sites: boron substitution for nitrogen (BN), Stone-Wales defects (SW), single boron vacancies (VB) and single nitrogen vacancies (VN). The binding energies are summarized in Table 2.

TABLE 2

Binding energy (in eV) of $C_2H_4$ on the defects of a (6x6) BN

| System | B/N | SW | $N_B$ | $B_N$ | $C_N$ | $C_B$ | $V_B$ | $V_N$ |
|---|---|---|---|---|---|---|---|---|
| Binding energy (eV) | NA* | −0.23 | NA | −1.95 | NA | NA | −3.71 | −1.90 |

*Not Available

Total Charge Density Analysis

The first step in hydrogenation, after chemisorption, is the reduction of the C—C bond order in ethene. A plot of total charge density of (A) $C_2H_4$, (B) $C_2H_6$, and (C) $C_2H_4$ molecule after adsorption on h-BN, SW, $V_N$ and $V_B$ defects, along the vertical plane passing through two carbon atoms of $C_2H_4$ molecule shows the reduction of this bond order (FIGS. 8A, 8B, and 8C). In the gas phase $C_2H_4$ is sp² hybridized (i.e., has a C=C bond), while $C_2H_6$ is sp³ hybridized (i.e., has a C—C bond). The total charge density of a $C_2H_4$ molecule on SW, VN and VB defects shows similarities with that of the gas phase of $C_2H_6$. The total charge density of $C_2H_4$ molecule on h-BN looks much more like that of single $C_2H_4$. This difference in bond order reduction is due to the fact that there are two distinct ways in which $C_2H_4$ can adsorb on defective h-BN surface: π and di-σ, as similarly discussed by Zaera (See, F. Zaera, "An Organometallic Guide to the Chemistry of Hydrocarbon Moieties on Transition Metal Surfaces." Chemical Reviews 95, 2651 (1995/12/01, 1995)). In the π-bonded mode, both carbons adsorb on top of a single atom of the substrate, as in chemisorption of $C_2H_4$ on a h-BN defect. In n-bonding the molecular sp2 hybridization is partly retained upon adsorption. In contrast, di-σ bonding results from the interaction of each carbon atom with a separate atom of the substrate (the substrate atoms can be the same or different species), as in the chemisorption of $C_2H_4$ on SW, $V_N$ and $V_B$ defects (See Table 3). Di-σ bonding is characterized by a sp3 rehybridization of C atomic orbitals.

TABLE 3

Binding Energy for ethene on h-BN, hydrogen on h-BN, ethene on platinum group metals, hydrogen on Pt(100), hydrogen on Pd(100), and hydrogen on Ni(100).

| | Binding Energy (eV) | |
|---|---|---|
| | Ethene | Hydrogen |
| h-BN | | |
| $V_B$ | −3.71 | −5.58 |
| $V_N$ | −1.90 | −1.64 |
| SW | −0.23 | 0.64 |
| Pt 100 | | |
| di sigma | −2.32 | −2.88 |
| pi-top | −1.55 | |
| Pd 100 | | |
| di sigma | −0.84 | −2.92 |
| pi-top | −0.33 | |
| Ni 100 | | |
| di sigma | −1.76 | −2.81 |
| pi-top | −0.82 | |

Hydrogenation in an Alumina Reactor with Zirconia Oxide Milling Media

Figure 9:
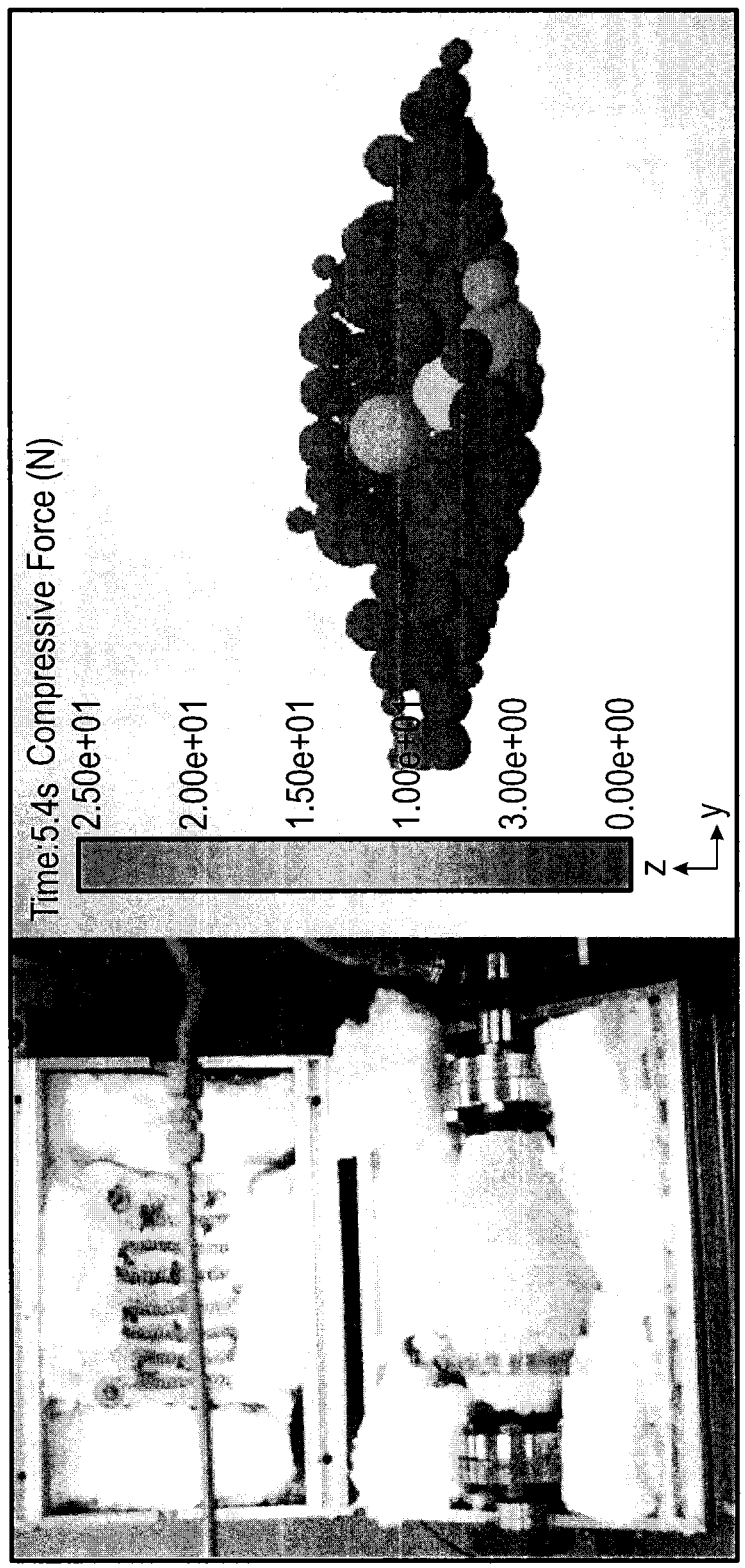
FIG. 9 (left) is an image of a pebble mill reaction vessel constructed of alumina and filled with $ZrO_2$ milling media. The sloped sides facilitate circulation of the catalyst. (Right) A simulation of the reactor shows the evolution of forces that occur. At 66 rpm, forces up to 25 N are realized.
Figure 10:
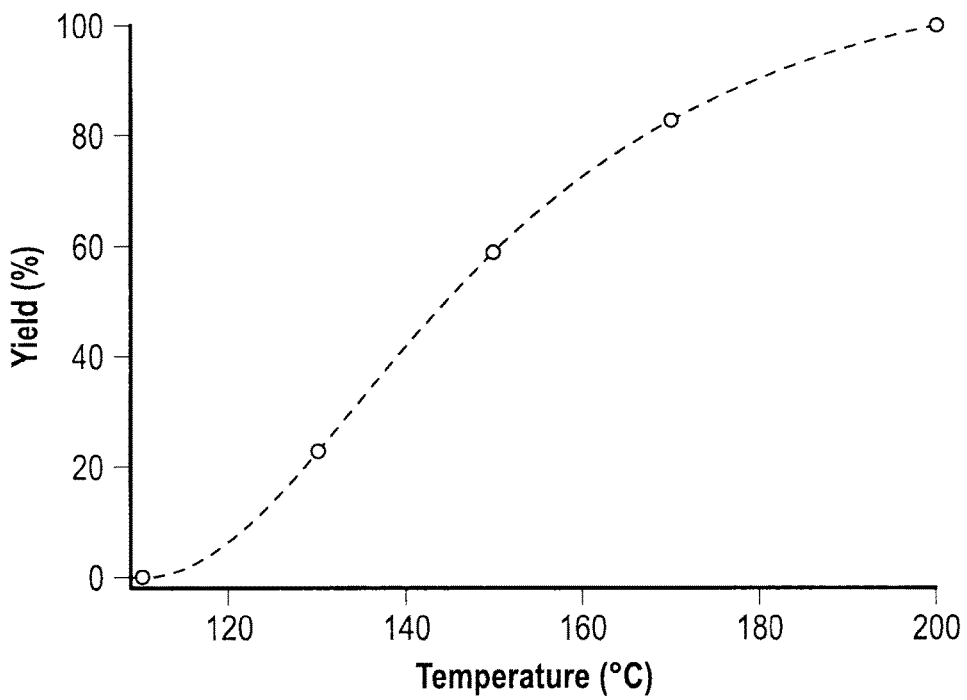
FIG. 10 is a graphical illustration of the relationship between temperature and the hydrogenation of propene. As temperature increases, the % yield of hydrogenated propene products increases.

As small amounts of metal impurities may lead to the observation of anomalous catalytic activity, a custom pebble mill, similar to the one made out of stainless steel described above, was constructed out of alumina (see FIG. 9) and tested using 700 grams of $ZrO_2$ milling media. This custom pebble mill was used to study the hydrogenation of specific substrates (5 g samples of each) in the presence of hydrogen and a defect laden h-BN catalyst (0.5 g sample). Final results were observed and calculated after 24 hours, as measured by GC/MS using the above described method (Table 4). As can be seen in Table 4 and illustrated in corresponding FIG. 10, propene exhibited increasing levels of hydrogenation as the temperature increased from 110° C. to 200° C. signifying that a relationship exists between temperature and hydrogenation.

Figure 11:
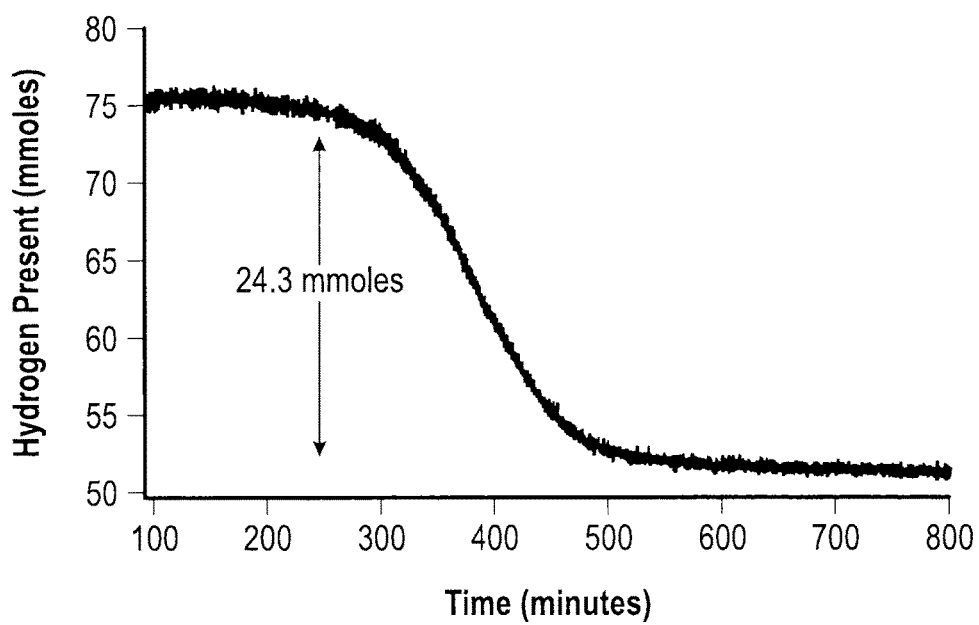
FIG. 11 is a graphical illustration of the hydrogen uptake of 27.7 mmol of (E)-stilbene in the presence of 0.5 g of dh-BN catalyst.

Hydrogenation uptake was observed as a pressure change correlating to a change in the hydrogen present over time, see e.g., FIG. 11, which illustrates that 27.7 mmol of (E)-stilbene had a hydrogen uptake of approximately 24.3 mmol hydrogen when using 0.5 g of defect laden h-BN catalyst. Additionally, the hydrogenation temperature was monitored and the % yield of hydrogenated substrates was measured (See Table 4). Although the defect laden h-BN catalyst did not possess any detectable amounts of iron or nickel, as measured by ICP-AES (Inductively Coupled Plasma Atomic Emission Spectroscopy), it is of note that propene gas was one of the substrates hydrogenated which reduces the amount of metals like nickel or iron that may be present in reagents. Additionally, an $H_2$/propene mixture was also tested without the presence of the defect laden h-BN catalyst and no measurable amounts of hydrogenation products were observed.

TABLE 4

Substrates investigated for hydrogenation over dh-BN after 24 hours.

| Compound | Structure | Boiling Point (° C.) | Hydrogenation Temperature (° C.) | Yield |
| --- | --- | --- | --- | --- |
| Propene | 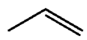 | −47.6 | 110-120 | 0% at 110° C., 23% at 130° C., 53% at 150° C., 99% at 170° C., 100% at 200° C. |
| Octadec-1-ene | 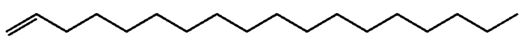 [SMILES: C=CCCCCCCCCCCCCCCCC] | 179 | 150 | 35% |
| 1,1-diphenylethene | 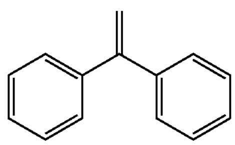 | 270 | 170 | 100% |
| (Z)-stilbene | 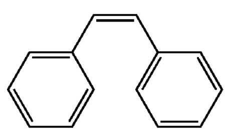 [SMILES: C(=C/c1ccccc1)/c1ccccc1] | 271 | 170 | 100% |
| (E)-stilbene | 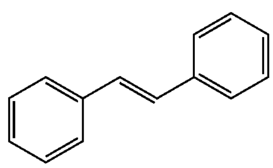 [SMILES: C(=C\c1ccccc1)/c1ccccc1] | 305 | 170 | 92.5% |
| (E)-cinnamic acid | 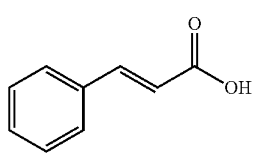 [SMILES: O=C(O)/C=C/c1ccccc1] | 300 | 170 | 45% |
| Chalcone | 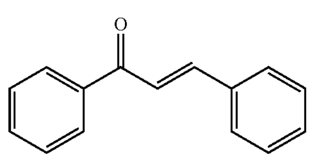 [SMILES: O=C(/C=C/c1ccccc1)c1ccccc1] | 330 | 240 | 100% |

From the above description, it is clear that the inventive concept(s) disclosed herein is well adapted to carry out the objects and to attain the advantages mentioned herein as well as those inherent in the inventive concept(s) disclosed herein. While exemplary embodiments of the inventive concept(s) disclosed herein have been described for purposes of this disclosure, it will be understood that numerous changes may be made which will readily suggest themselves to those skilled in the art and which are accomplished without departing from the scope of the inventive concept(s) disclosed herein and defined by the appended claims.

What is claimed is:

1. A heterogeneous hydrogenation catalyst, comprising:
   a solid surface substantially free of metals, the solid surface having at least one Lewis acid site and at least one Lewis base site; and
   at least one defect frustrating at least one pair of Lewis acid and Lewis base sites, wherein the at least one frustrated pair of Lewis acid and Lewis base sites is catalytically active;
   wherein the Lewis acids are selected from the group consisting of Group 13 elements in a trigonal planar configuration, halides of Group 15 elements, electron poor π-systems, and combinations thereof, and wherein the Lewis bases are selected from the group consisting of simple anions, lone-pair containing species, complex anions, electron rich π-systems, and combinations thereof.

2. A heterogeneous hydrogenation catalyst, comprising:
   a solid surface having non-metallic Lewis acid moieties and non-metallic Lewis base moieties spaced a distance apart from one another such that (a) catalytic activity is present therebetween and (b) the formation of an acid-base adduct is prevented;

wherein the Lewis acid moieties are selected from the group consisting of Group 13 elements in a trigonal planar configuration, halides of Group 15 elements, electron poor π-systems, and combinations thereof, and wherein the Lewis base moieties are selected from the group consisting of simple anions, lone-pair-containing species, complex anions, electron rich π-systems, and combinations thereof.

3. The heterogeneous hydrogenation catalyst of claim 2, wherein the Lewis acid moiety is a Group 13 element in a trigonal planar configuration and the Lewis base moiety is a lone-pair containing species.

4. The heterogeneous hydrogenation catalyst of claim 2, wherein the hydrogenation catalyst at least partially comprises hexagonal boron nitride.

5. A heterogeneous hydrogenation catalyst, comprising:
a sheet of catalytically active material substantially free of metals having unsatisfied Lewis acid-base pairs along a surface of the sheet;

wherein the Lewis acids are selected from the group consisting of Group 13 elements in a trigonal planar configuration, halides of Group 15 elements, electron poor π-systems, and combinations thereof, and wherein the Lewis bases are selected from the group consisting of simple anions, lone-pair containing species, complex anions, electron rich π-systems, and combinations thereof.

6. The heterogeneous hydrogenation catalyst of claim 5, wherein the heterogeneous hydrogenation catalyst comprises hexagonal boron nitride having at least one catalytically active defect on a surface thereof, wherein the hexagonal boron nitride is substantially free of metals.

7. The heterogeneous hydrogenation catalyst of claim 6, wherein the catalytically active defect Is selected from the group consisting of Stone-Wales defects, B/N defects, boron substituted nitrogen, nitrogen substituted for boron, carbon substituted for nitrogen, carbon substituted for boron, boron vacancy, nitrogen vacancy, and combinations thereof.

8. The heterogeneous hydrogenation catalyst of claim 5, wherein the catalyst is capable of catalytically hydrogenating an alkene.

9. A hydrogenation process comprising:
contacting a hydrogenatable compound with hydrogen gas and a catalyst in a reactor, wherein the catalyst comprises a solid material having at least one frustrated Lewis acid-base pair; and
catalytically hydrogenating the hydrogenatable compound;

wherein the Lewis acids are selected from the group consisting of Group 13 elements in a trigonal planar configuration, halides of Group 15 elements, electron poor π-systems, and combinations thereof, and wherein the Lewis bases are selected from the group consisting of simple anions, lone-pair containing species, complex anions, electron rich π-systems, and combinations thereof.

10. The process of claim 9, wherein the hydrogenatable compound is a compound having functional groups selected from the group consisting of alkene, alkyne, aldehyde, ketone, ester, imine, amide, nitrile, nitro, and combinations thereof.

11. The process of claim 9, further wherein the solid material having at least one frustrated Lewis pair comprises a solid surface substantially free of metals, the solid surface having at least one Lewis acid site and at least one Lewis base site, and at least one defect frustrating at least one pair of Lewis acid and Lewis base sites, wherein the at least one frustrated pair of Lewis acid and Lewis base sites is catalytically active.

12. The process of claim 9, further wherein the solid material having at least one frustrated Lewis pair comprises a solid surface having non-metallic Lewis acid moieties and non-metallic Lewis base moieties spaced a distance apart from one another such that (a) catalytic activity is present therebetween and (b) the formation of an acid-base adduct therefrom is prevented.

13. The process of claim 12, wherein the Lewis acid moiety is a Group 13 element in a trigonal planar configuration and the Lewis base moiety is a lone-pair containing species.

14. The process of claim 12, wherein the hydrogenation catalyst at least partially comprises hexagonal boron nitride.

15. The process of claim 9, further wherein the catalyst comprises a sheet of catalytically active material substantially free of metals having unsatisfied Lewis acid-base pairs along a surface of the sheet.

16. The process of claim 9, wherein the catalyst comprises hexagonal boron nitride having a catalytically active defect on a surface thereof, wherein the hexagonal boron nitride is substantially free of metals.

17. The process of claim 16, wherein the catalytically active defect is selected from the group consisting of Stone-Wales defects, B/N defects, boron substituted for nitrogen, nitrogen substituted for boron, carbon substituted for nitrogen, carbon substituted for boron, boron vacancy, nitrogen vacancy, and combinations thereof.

18. The process of claim 9, wherein the catalyst is capable of catalytically hydrogenating an alkene.

19. The heterogeneous hydrogenation catalyst of claim 1, wherein the heterogeneous hydrogenation catalyst comprises hexagonal boron nitride having at least one catalytically active defect on a surface thereof, wherein the hexagonal boron nitride is substantially free of metals.

20. The heterogeneous hydrogenation catalyst of claim 19, wherein the catalytically active defect is selected from the group consisting of Stone-Wales defects, B/N defects, boron substituted nitrogen, nitrogen substituted for boron, carbon substituted for nitrogen, carbon substituted for boron, boron vacancy, nitrogen vacancy, and combinations thereof.

21. The heterogeneous hydrogenation catalyst of claim 1, wherein the catalyst is capable of catalytically hydrogenating an alkene.

22. The heterogeneous hydrogenation catalyst of claim 2, wherein the heterogeneous hydrogenation catalyst comprises hexagonal boron nitride having at least one catalytically active defect on a surface thereof, wherein the hexagonal boron nitride is substantially free of metals.

23. The heterogeneous hydrogenation catalyst of claim 22, wherein the catalytically active defect is selected from the group consisting of Stone-Wales defects, B/N defects, boron substituted nitrogen, nitrogen substituted for boron, carbon substituted for nitrogen, carbon substituted for boron, boron vacancy, nitrogen vacancy, and combinations thereof.

24. The heterogeneous hydrogenation catalyst of claim 2, wherein the catalyst is capable of catalytically hydrogenating an alkene.

* * * * *

UNITED STATES PATENT AND TRADEMARK OFFICE
CERTIFICATE OF CORRECTION

PATENT NO. : 10,329,234 B2
APPLICATION NO. : 15/670732
DATED : June 25, 2019
INVENTOR(S) : Richard G. Blair Page 1 of 1

It is certified that error appears in the above-identified patent and that said Letters Patent is hereby corrected as shown below:

In the Specification

Column 11, Line 35: Delete "PCTFS," and replace with -- PCTF5, --

Column 14, Line 9: Delete "n-bonding" and replace with -- π-bonding --

Signed and Sealed this
Third Day of September, 2019

Andrei Iancu
*Director of the United States Patent and Trademark Office*